United States Patent [19]

Comeau et al.

[11] Patent Number: 4,735,609
[45] Date of Patent: Apr. 5, 1988

[54] IV FLUID WARMER

[75] Inventors: Perry J. Comeau, Overland Park; Thomas N. Tietze, Olathe, both of Kans.

[73] Assignee: Medical Industrial Technologies, Inc., Overland Park, Kans.

[21] Appl. No.: 888,965

[22] Filed: Jul. 24, 1986

[51] Int. Cl.$^4$ .............................................. A61F 7/12
[52] U.S. Cl. ................................. 604/114; 128/400; 165/170; 165/174
[58] Field of Search .................. 128/399, 400, 403; 219/299, 302, 305; 165/170, 174; 604/113, 114, 408–410; 126/447, 448

[56] References Cited

U.S. PATENT DOCUMENTS

| Re. 27,100 | 3/1971 | De Wall | 128/400 |
|---|---|---|---|
| 3,485,245 | 12/1969 | Lahr et al. | 604/408 |
| 3,612,059 | 10/1971 | Ersek | 604/113 |
| 4,122,828 | 10/1978 | Di Peri | 165/170 |
| 4,167,663 | 9/1979 | Grazow, Jr. et al. | 604/114 |
| 4,291,675 | 9/1981 | Rahman | 126/447 |

FOREIGN PATENT DOCUMENTS 2403082 5/1979 France ......................... 219/302

OTHER PUBLICATIONS

Y. C. Fung, "*Biodynamics Circulation*", 1984, pp. 10–12, Publisher-Springer-Verlag, New York.

*Primary Examiner*—Stephen C. Pellegrino
*Assistant Examiner*—Ralph Lewis
*Attorney, Agent, or Firm*—Head & Johnson

[57] ABSTRACT

This fluid warmer includes a disposable pouch and a pouch warmer assembly. The pouch has an inlet and an outlet and in between there is a plurality of ribs which are so arranged as to force equal flow across the bottom heating area of the pouch. The pouch is insertable into a warmer assembly which consists of a housing which provides mechanical support for the heating element, temperature regulating circuit board, and an arrangement to maintain thermal contact between the heating element and the pouch. The posterior surface of the pouch will be constructed of a metal possibly coated with Teflon for rapid heat conduction from the heating element. The metals may be stainless steel, aluminum and copper or medical aloids.

8 Claims, 4 Drawing Sheets

IV FLUID WARMER

FIELD OF THE INVENTION

This invention is concerned with the field of heating fluids such as warming IV (intravenous) fluids for children and adults.

The flow of various fluids is widely used in the medical treatment of patients or for that matter in the practice of veterinary medicine. One of the most widely known fluid systems in medical treatment is the use of intravenous (IV) feeding of children and adults to provide both water and food to the patient. Irrigation solution is also used for arthoscopic surgery. In these systems fluid is placed in lines under pressure, either from an elevated container as is common in IV application or by use of pumps. The fluid which flows through these lines are conducted into the human body, most commonly by injecting a hollow needle into the veins.

It is considered that many of these fluids should be warmed to a selected temperature. However, if they are warmed it should be under strict controlled conditions. It is therefore an object of may invention to provide a fluid warmer for warming fluids used in medical treatment. It is another object of my invention to provide a fluid warmer that uniformly heats the fluid flowing through the warmer.

SUMMARY OF THE INVENTION

This fluid warmer is composed of two major parts: (1) a disposable pouch and (2) a warmer assembly for the pouch. The pouch has an inlet and an outlet which is connected to the flow line of a fluid being used in medical treatment. The shape of the pouch is generally rectangular with two ends and two sides. There is provided a plurality of baffles or ribs, each of which extends from near one side of the pouch to near the other side. There is an entrance manifold area or space along one side of the baffles and an exit manifold along the other side between the ends of the ribs and the side of the pouch. These ribs extend from the bottom to the top so as to form flow channels. The variation of size of orifice or open spaces between adjacent ribs guarantees the even flow of fluid across the heated area by virtue of Poisiville's formula.

These ribs in the heated area of the pouch evenly distributed fluid flow from the supply manifold to the exit manifold.

There is a warmer assembly for receiving the disposable pouch. It includes a housing which provides mechanical support for a heating element and a temperature regulating circuit board. The housing is so designed as to allow for easy installation and removal of the pouch from the housing without removing the pouch from the flow lines into which it has been connected.

Various other objects and a better understanding of the invention will be had from the following description taken in conjunction with the drawings.

DETAILED DESCRIPTION OF THE INVENTION

Figure 1:
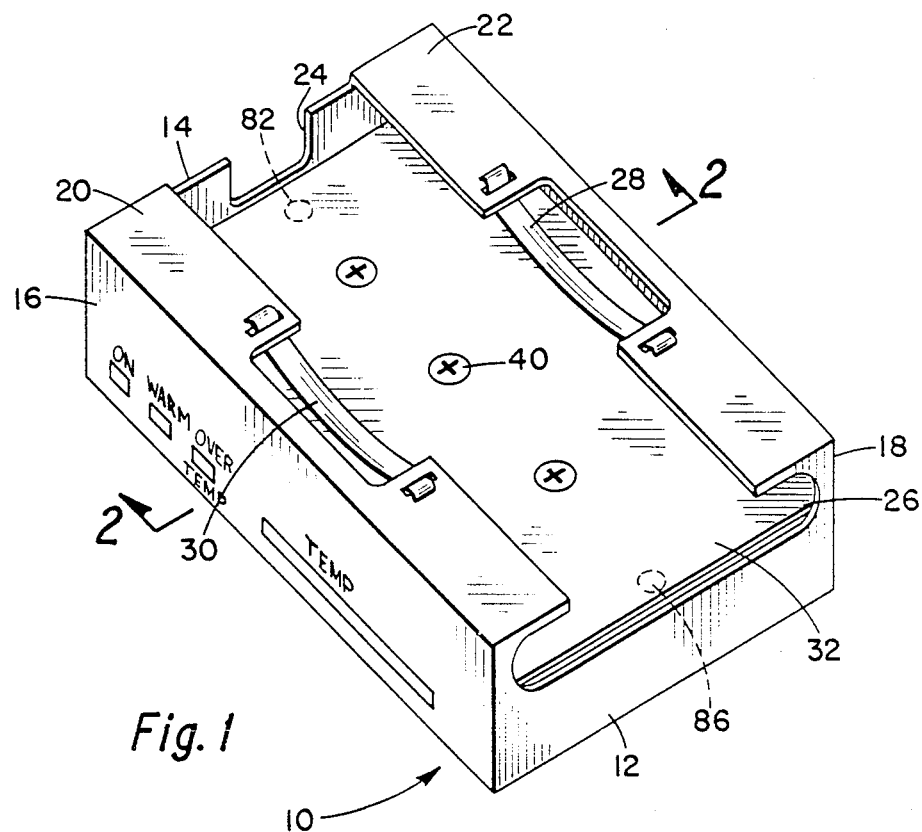
FIG. 1 is an isometric view of the warmer assembly.

The invention includes a warming assembly and a disposable pouch. The warming assembly as shown in FIG. 1, the pouch in FIGS. 3 and 4, and the two assembled together shown in FIG. 2. Turning first to FIG. 1, there is shown a warmer assembly 10 which includes a rectangular box-like structure having a first end 12, a second end 14, a front or first side 16, and a rear side 18. It also has a first top strip 20 and a second top strip 22. End 14 has a small cut-out 24 and end 12 has a cut-out 26 which is nearly the entire width of the end 12. Containment springs 28 and 30 are also provided in top strips 22 and 20 respectively. As shown also in FIG. 2, a heat dissipation panel 32 is provided inside the warmer assembly at about the level of the bottom of openings 26 and 24. This panel 32 is supported on top of heater 36 which in turn is supported from support panel 38 by a plurality of screws 40 and spacers 42. Support panel 38 is supported from the bottom of the warmer assembly by hardware 44.

Figure 2:
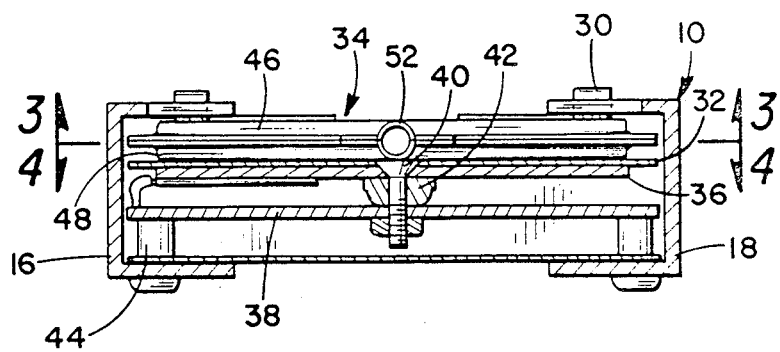
FIG. 2 is a view taken along the line 2—2 of FIG. 1.
Figure 4:
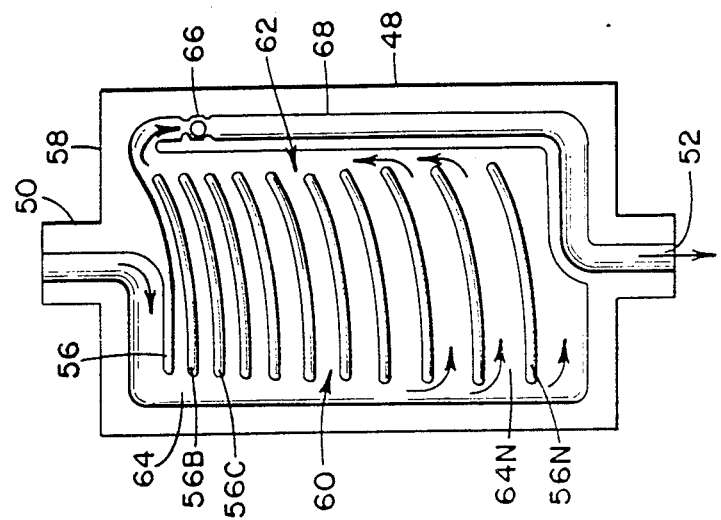
FIG. 4 is a view taken along the line 4—4 of FIG. 2.
Figure 3:
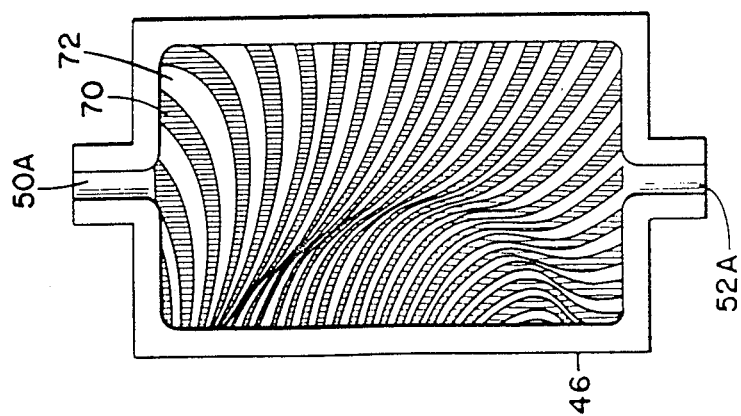
FIG. 3 is a view of the top of the disposable pouch taken along the line 3—3 of FIG. 2.

The pouch 34 shown in FIG. 2 has a top portion 46 and a bottom portion 48. The flat part of bottom portion 48 is preferably made of metal such as stainless steel. The heat tranfer through metal makes this design unique compared to previous and other pouches. The top portion 46 is shown in FIG. 3 and the bottom portion 48 is shown in FIG. 4. The view of both FIGS. 3 and 4 are from the inside looking out. That is, with the orientation of FIG. 2, FIG. 3 is a view looking up and FIG. 4 is a view looking down.

Turning now to FIG. 4, there is shown the bottom portion 48 having an inlet portion 50 and an outlet portion 52. There is a plurality of ribs 56 through 56N. 56 curves slightly and is in integrally formed with the end 58 of the pouch. The first ends of the ribs 56 are essentially aligned leaving at entrance manifold area 60. The second ends of ribs 56 are also generally aligned and leave an exit manifold area 62. These ribs are generally parallel. However, the spacing between the adjacent ribs 56 continually increases from the top spacing 64 to the bottom 64N. When the top portion or cover 46 is placed on top of the bottom portion 48, the ribs 56 are in contact with the top portion. Thus all fluid flows in the channels between the ribs. In other words, the fluid flows from the entrance manifold area 60 to the exit manifold area 62. The orifices or openings between the ribs 56 are such as to guarantee the even flow fluid across the heated area by virtue of Poiseville's theorem which is used to size the orifices using known mathematical methods. As shown the size of openings of space 64 increases from space 64 to space 64N to assure even flow across the heated area in contact with heat dissipation panel 32. Fluid flows generally as indicated by the arrows in FIG. 4 and passes through a check valve 66 and down tube 68 to outlet 52. Check valve or one way valve 66 prevents retrograde movement of fluid.

Attention is redirected to FIG. 3 which shows the top 46 of the disposable heating pouch. This includes a plurality of heat reflective zones 70 and visual zones 72. The heat reflective area or zone 70 will improve the efficiency of the heating. The visual zones 72 are so designed that visual inspection of fluid flow in general is possible. The bottom 48 of FIG. 4 and the top portion 46 of FIG. 3 are placed together as indicated in FIG. 2 and are secured together by any well known means. The material of which these are made will be any material which is inactive in the presence of the fluid being heated so as not to contaminate such fluid or damage the pouch. The inlet and outlet are connected into the medical fluid supply line. The housing is so designed as to allow for easy installation or removal of the pouch and corresponding tubing from the warmer assembly without removing the pouch from the flow line. This is apparent from FIGS. 1 and 2. The flow line extends out opening 24 of end 14 when the first end of the pouch enters opening 32 which is large enough to accomodate it. The pouch is continued to be inserted until the pouch is completely within the warmer assembly. The pouch is held in position by containment springs 28 and 30 and strips 20 and 22. The pouch, the flow lines and related equipment can all be assembled and then the pouch can be inserted into the warmer assembly of FIG. 1.

As shown in FIGS. 1 and 2, there is a heating element beneath heat dissipation 32. We will now discuss the heating controls.

The heating unit must heat the fluid flowing through the disposable pouch and regulate the temperature of the fluid exiting the pouch within a required degree of accuracy. Means should also be provided to indicate over temperature status and the special temperature of the heated fluid. The heating discussed below and illustrated in FIG. 5 is a particularly suitable circuit and will display negative fluid tempertures as well as temperatures as high as 199.9 degrees Fahrenheit.

Figure 6:
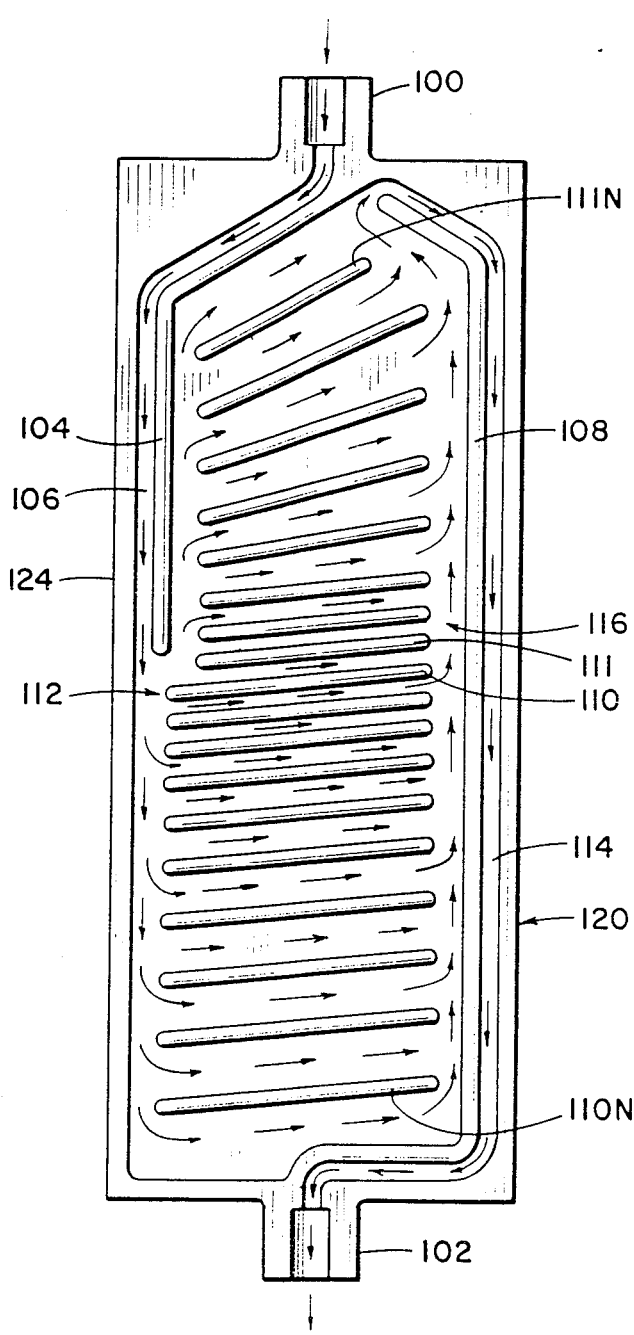
FIG. 6 is a view similar to that of FIG. 4 of a different embodiment.

Attention is next directed to FIG. 6, whichis a different embodiment of the arrangement of the ribs and may be considered an elongated version of that embodiment shown in FIG. 4. There is shown a bottom portion 120 having an inlet portion 100 and an outlet portion 102. There is a diverter wall 104 which extends from the inlet portion to about midway of the bottom portion 120. This forms a flow channel 106. There is a plurality of ribs mounted within the bottom portion 120 and for convenience of description is divided into a first or upper group of ribs 111 through 111N and a second or lower group of ribs 110 to 110N. There is thus formed an entrance manifold 112 between the ends of the ribs and the diverter wall 104 and wall 124. There is an exit manifold 116 between the ends as shown on the right-hand side of the drawing and the wall 108. The opening between the ribs 110 and 111 continually increase from the middle to the ends of the apparatus. Similarly, with the device shown in FIG. 4 when a top portion is placed on top of the bottom portion 120 the ribs 111 and 110, diverter wall 104 and wall 108 are all in contact with the top portion. Thus, all fluid flows in through flow channel 106, the channels between the ribs and exit channel 114. Thus fluid flow from the entrance manifold area 112 to the exit manifold area 116. The orifices openings between the ribs 111 and 110 are such as to guarantee the even flow of fluid across the heated area by virtue of Poiseville's therein which is used to size the orifices between the ribs using known mathematical methods. In use, the pouch of FIG. 6 will normally be hung in a position such that the inlet portion 100 is at the top and the outlet portion 102 is at the bottom. The exit, thus positioned at the top of the pouch, will allow quick escape of air when the pouch fills.

Figure 5:
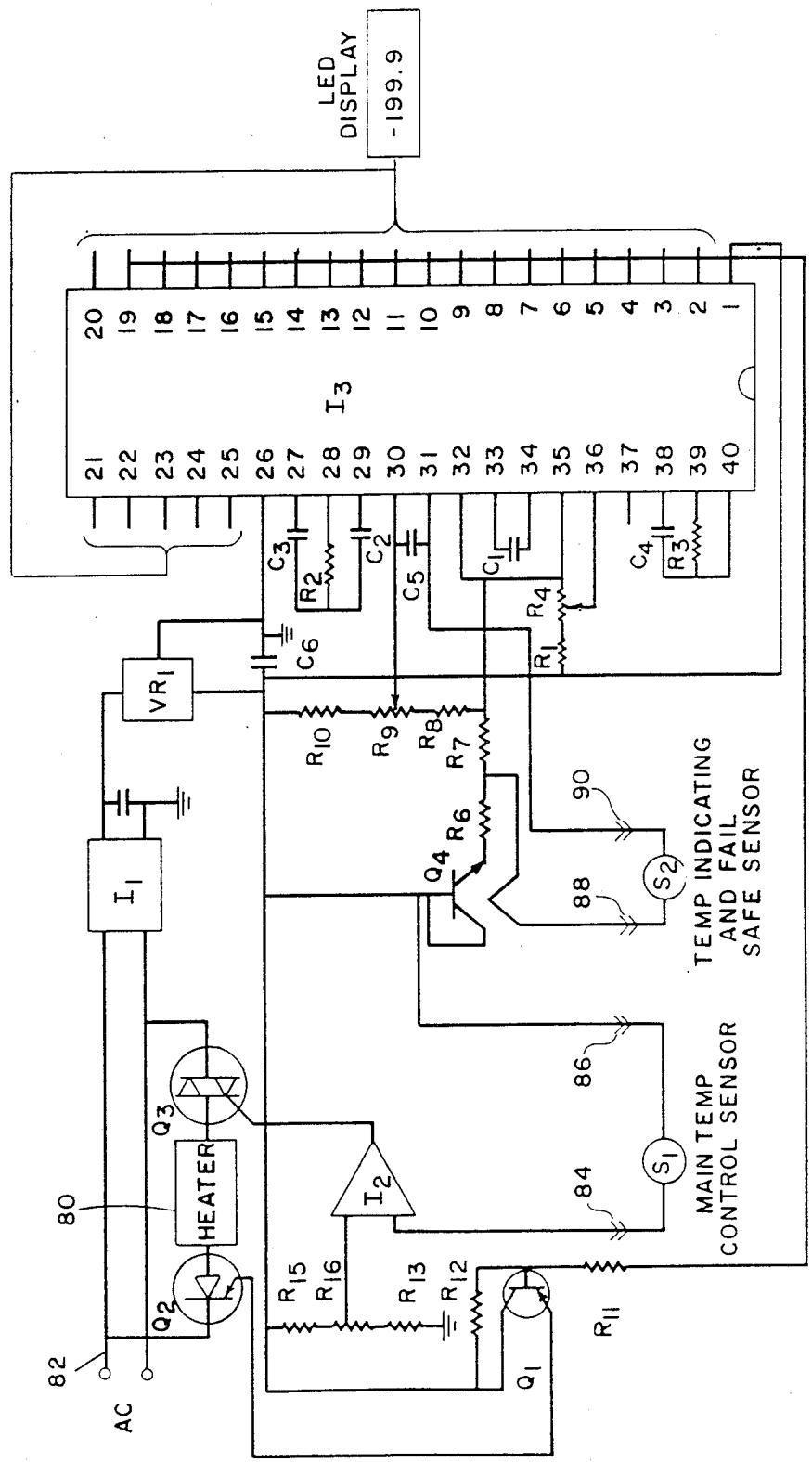
FIG. 5 is a control circuit diagram.

Referring to FIG. 5, the heating unit is comprised of heating circuitry, failsafe circuitry and a temperature measuring circuit. The heating circuitry controls the electrical current supplied to heater 80 and includes thyristor Q3, amplifier I2, temperature sensor S1, and resistors R13, R14 and R15. R14 is the fine adjustment for calibration of the heating temperature. Amplifier I2 is controlled by resistor R14 and sensor S1 and provides the control voltages for thyristor Q3. Thyristor Q3 controls the AC current flow from the AC current source 82 into the heater 82.

The failsafe circuitry provides over-temperature shutdown of heater 82. If Thyristor Q3 malfunctions and includes transistor Q1, thyristor Q2 and resistors R11, R12. Transistor Q1 is triggered by an over-temperature signal from the temperature measuring circuit to turn off thyristor Q2 and thereby turn off the heater H1.

The temperature measuring circuit measures and displays the temperature at sensor S2 and includes resistors R1 through R10, capacitors C1 through C6, sensor S2, transistor Q4 and analog-to-digital converter I3. Converter I3 is a 3½ digit direct display drive analog-to-digital converter set up in a temperature measurement mode. It is made by Teledyne Semiconductor Corporation (TSC7107A).

Sensors S1 and S2 can be molded into the disposable pouch and connected to the heating unit by connectors at 84, 86, 88, 90. The connections are made when the disposable pouch is inserted into the heating unit.

Amplifier I1, voltage regulator VR1 and a tranformer (not illustrated) compose the power supply.

Our invention can have many operations and applications. Some of the warm fluid applications are:
1. Warming of IV's in children and adults.
2. Warming of cyctoscopy fluids during TURP and for cysto in children and adults.
3. Warming of irrigation balance salt solution during eye opthamology surgery.
4. Warming of irrigation solution for arthoscopic surgery.
5. Total joint replacement irrigation.
6. Irrigation of wound dibriment surgery such as in burn and infection cases and abdominal peritonitis.
7. Warming of antibiotic and chemotherapy solutions given in home health care setting.
8. Warming of protein replacement solutions given by subclavian catheter.
9. Warming of tube feedings given to patients unable to eat by conventional means.
10. The warming of blood.
11. Applications as dictated by veterinary medicine.
12. Warming of fluids and medication for epidural injection.
13. For fluids to be exchanged in parteneal dialysis.

While the invention has been described with a certain degree of particularity, it is manifest that many changes may be made in the details of construction and the arrangement of components without departing from the spirit and scope of this disclosure. It is understood that the invention is not but is to be limited only by the scope of the attached claim or claims, including the full range of equivalency to which each element thereof is entitled.

What is claimed is:
1. A disposable pouch for use in heating a flowing volume of fluid which comprises:
   an inlet;
   an outlet;
   a top portion;

a bottom portion which together with said top portion forms an enclosed space having a first side and a second side;

a plurality of unevenly spaced ribs extending between said top portion and said bottom portion, each said rib having a first end and a second end, said first ends being spaced from the first side of said enclosed space to form an entrance manifold area and the second ends all being spaced from the second side of said enclosed space to form an exit manifold area, the distance between adjacent pairs of first ends of said rib increasing from said inlet end to said outlet end so as to obtain even flow throughout said space, the space between said ribs together with said manifold area forming a flow path between said inlet and said outlet; and a one way valve in said flow path.

2. A disposable pouch as defined in claim 1 in which the plurality of ribs are spaced from each other in a pattern to provide a substantially even flow rate for each unit of space between the said ribs.

3. A disposable pouch as defined in claim 1 in which the plurality of ribs are spaced in order to create increased fluid surface area and specific fluid circulation in order to allow warming.

4. A disposable pouch as defined in claim 1 in which said top portion has a plurality of heat reflective zones with visual zones dispersed between such heat reflective zones such that one can visually observe the fluid throughout the pouch.

5. A heating assembly for a disposable pouch having an inlet, an outlet, a width and a length which comprises:

a rectangular-like box having a first side, a second side, a first end, a second end, a bottom and a top, said first end having an opening wider than said pouch width and the second end having an opening narrower than the pouch width;

said top of said box having therein a narrow member along each side thereof leaving open space therebetween and containment springs mounted in each narrow member;

a heat dissipation panel supported between said sides and said ends at a position at about the level of the said first opening and said second opening;

a heater element positioned below said heat dissipation panel; and means to control said heater.

6. A disposable pouch and heating assembly for use in heating a flowing volume of fluid which comprises:

a pouch inlet;

a pouch outlet;

a pouch top portion;

a pouch bottom portion which together with said top portion forms an enclosed space having a pouch width and having a first side and a second side and a first end and a second end;

a plurality of unevenly spaced pouch ribs, each said rib having a first end and second end, said first ends being spaced from the first side of said enclosed space to form an entrance manifold area and the second ends being spaced from the second side of said enclosed space to form an exit manifold area, the distance between adjacent pair of first ends of said ribs increasing from said pouch inlet end to said pouch outlet end so as to obtain an even flow throughout said space, the space between said ribs together with said manifold areas forming a flow path between said pouch inlet and said pouch outlet;

a rectangular like box having a first side, a second side, a first end, a second end, a bottom and a top, said first end having an opening wider than said pouch width and a second end having an opening narrower than the pouch width;

said top of said box having a narrow member along each side thereof leaving an open space therebetween;

containment springs mounted in each said narrow member;

a heat dissipation panel supported between said sides of said box and at a position about the level of the said first opening and said second opening;

a heater element positioned below said heat dissipation panel and means to control said heater.

7. A disposable pouch as defined in claim 6 in which said bottom portion is made of stainless steel.

8. A disposable pouch for use in heating a flowing volume of fluid which comprises:

an inlet;

an outlet;

a top portion;

a bottom portion, which together with said top portion forms an enclosed space having a first side and a second side, said bottom portion having a first diverter wall extending from the inlet to about midway of the bottom portion between the inlet and the outlet and forming a flow channel;

an exit flow channel extending from near said outlet to said inlet portion;

a first set of unevenly spaced ribs extending between said top portion and said bottom portion, each rib of said first set having a first end and a second end, said first ends being spaced from the diverter wall to form a portion of an entrance manifold and the second ends being spaced from said flow channel to form part of an exit manifold area, the distance between adjacent pairs of said first ends of said first ribs at said first set increasing from said middle portion to the outlet end so as to obtain even flow through said spaces;

a second set of unevenly spaced ribs extending between said top portion of said ribs and said bottom portion, each said rib of said second set having a first end and a second end, said first end being spaced from a first side of said enclosed space to form a part of the entrance manifold area and the second ends all being spaced from the second side of the enclosed space to form a part of an exit manifold area, the distance between adjacent pairs at first ends of said ribs increasing from said center portion to the outlet end so as to obtain even flow throughout such space.

* * * * *